United States Patent [19]
Andriollo et al.

[11] Patent Number: 5,350,521
[45] Date of Patent: Sep. 27, 1994

[54] PROCESS FOR SEPARATING CATALYSTS FROM ORGANIC SOLUTIONS, BY MEANS OF SEMIPERMEABLE MEMBRANES

[75] Inventors: Nunzio Andriollo, Bollate; Giorgio Cassani, Arluno; Paolo D'Olimpio, Novara; Bruno Donno, Novara; Marco Ricci, Novara, all of Italy

[73] Assignee: Eniricerche, S.p.A., Milan, Italy

[21] Appl. No.: 111,280

[22] Filed: Aug. 24, 1993

[30] Foreign Application Priority Data

Sep. 1, 1992 [IT] Italy .................. MI92 A 002039

[51] Int. Cl.$^5$ .............................................. B01D 61/00
[52] U.S. Cl. .................................. 210/653; 210/650; 210/651; 210/654
[58] Field of Search ............ 210/650, 651, 653, 500.25, 210/654, 500.27; 423/DIG. 13, 140

[56] References Cited

U.S. PATENT DOCUMENTS

| | | |
|---|---|---|
| 3,617,553 | 11/1971 | Westaway et al. ................ 210/651 |
| 4,311,521 | 1/1982 | Harper et al. ....................... 423/140 |
| 4,731,482 | 8/1967 | Veniurello et al. . |
| 4,855,491 | 8/1989 | Chew et al. ..................... 210/500.3 |
| 5,215,667 | 6/1993 | Livingston, Jr. et al. .......... 210/651 |

FOREIGN PATENT DOCUMENTS

0263953  8/1987  European Pat. Off. .

*Primary Examiner*—Robert A. Dawson
*Assistant Examiner*—Ana M. Fortuna
*Attorney, Agent, or Firm*—Rogers & Wells

[57] ABSTRACT

Disclosed is a process for separating metal catalysts based on ammonium and phosphonium phosphotungstates from reaction mixtures in which they are dissolved. The process is based on the use of semipermeable membranes and has found an useful application in the separation of the above said catalysts from mixtures obtained from alkenes and soybean oil epoxidation.

18 Claims, 2 Drawing Sheets

PROCESS FOR SEPARATING CATALYSTS FROM ORGANIC SOLUTIONS, BY MEANS OF SEMIPERMEABLE MEMBRANES

The present invention relates to a process for separating catalysts based on ammonium and phosphonium phosphotungstates from reaction mixtures in which they are dissolved, which process consists in treating said mixtures by means of ultrafiltration units equipped with semipermeable membranes.

It is well known that, in the catalytic processes, the use of homogeneous phase catalyst supplies, as compared to the use of heterogeneous phase catalysts, several advantages, such as, e.g., milder reaction conditions and a greater selectivity.

However, the use of homogeneous catalysis in organic synthesis processes not always can be applied owing to the difficulties which are met in the separation and recovery of said catalysts from the reaction mixtures.

In fact, the use of conventional techniques known in the art of separations, supplied often unsatisfactory results, thus limiting the development of the processes which take place under homogeneous catalysis conditions.

The problems arising during the separation processes are of several kinds and depend on the used techniques.

The precipitation, for example, requires a large number of processing steps and, when as precipitating agents non-solvents are used, it may imply the presence of toxic and/or flammable products.

The distillation makes it possible satisfactory separations of the various components of reaction mixtures to be obtained but, on the other hand, said components can undergo degradation phenomena owing to their long standing at high temperatures. Furthermore, the distillation requires high costs for purchasing the distillation facilities and owing to energy consumptions.

The chromatographic techniques such as, e.g., adsorbtion or ionic exchange become difficultly applicable when one tries to apply them on a large commercial scale.

The separation by extraction requires, like precipitation, further process steps and, generally, the use of toxic and/or flammable products.

The developement of separation technologies based on ultrafiltration made it possible the above drawbacks to be overcome or reduced, in particular such technologies display the following advantages:

they make it possible the addition to the reaction mixture to be avoided of other products (including toxic and/or flammable solvents) which, in most cases, must be separated during a later step;
they make it possible submitting heat sensible compounds to an excessive heating to be avoided;
they require a reduced energy consumption, above all as compared to distillation;
they require short operating times;
they require relatively low facility purchasing and maintenance costs;
they allow an easy scaling flexibility;
they make it possible high-molecular weight compounds (pigments, oligomers, polymers, degradation products, and so forth) possibly present in the reaction mixture, to removed besides the catalysts.

On the contrary, the development of such processes requires further that investigations are carried out into basic knowledge such as, e.g., the catalyst aggregation state in the several organic phases in view of a proper selection of membranes to be used.

In scientific literature, some processes are reported for separating catalysts from reaction mixtures by means of the use of semipermeable membranes: e.g., E.P. patent 0 263 953 B1 describes the separation by membranes, in aqueous media, of metal catalysts complexes, with water-soluble phosphines.

In its turn, U.S. Pat. No. 4,855,491 discloses the separation of metal catalysts and possibly present impurities, by means of the use of organic membranes, by reverse osmosis. In this case, the mixtures submitted to the treatment contain high water levels.

Also described are systems which allow the selective permeation of metal ions to be carried out from an aqueous/organic mixture towards an aqueous phase, through a semipermeable membrane which separates said phases (U.S. Pat. No. 4,311,521).

However, the methods known from pertinent technical literature are not generally applicable and, in particular, they do not teach to separate metal catalysts in homogeneous phase in the case of completely organic phases.

The present Applicant has found now that the above said catalysts can be separated in an advantageous way from the organic solutions in which they are dissolved.

In its widest aspect, the present invention relates to a process for separating catalysts constituted by an anionic portion based on phosphotungstates or arsenotungstates and a counterion with surfactant character based on ammonium or phosphonium salts, from the organic solutions in which they are dissolved, characterized in that the organic solutions are submitted to ultrafiltration in devices equipped with semipermeable membranes.

In the specific case according to the present invention, the dissolution of the catalyst is obtained by using counter-ions with surfactant character.

The results illustrated in the examples confirmed the previously cited advantages of this technology and its applicability at a technical level.

It was furthermore observed that the capability of the membranes, of retaining also other high molecular weight impurities, makes it possible the quality of the products to be improved, and the inorganic character of some of said membranes makes it possible the process to be carried out at high temperatures.

In general, the possibility of selectively separating, by means of semipermeable membranes, organic molecules contained in a solution strictly depends on both the nature of the membranes and the characteristics of the solution.

The preliminary investigations related to the determination of the suitable exclusion molecular weight (=that molecular weight at which the fractionation occurs) for the purpose of optimizing the permeate fluxes and the type of molecules which can flow through the selected membrane.

For that purpose, the tests were carried out on a system constituted by flat membranes in a static cell which, thanks to the simplicity of the equipment, makes it possible the several membranes to be rapidly evaluated.

DETAILED DESCRIPTION

Figure 1:
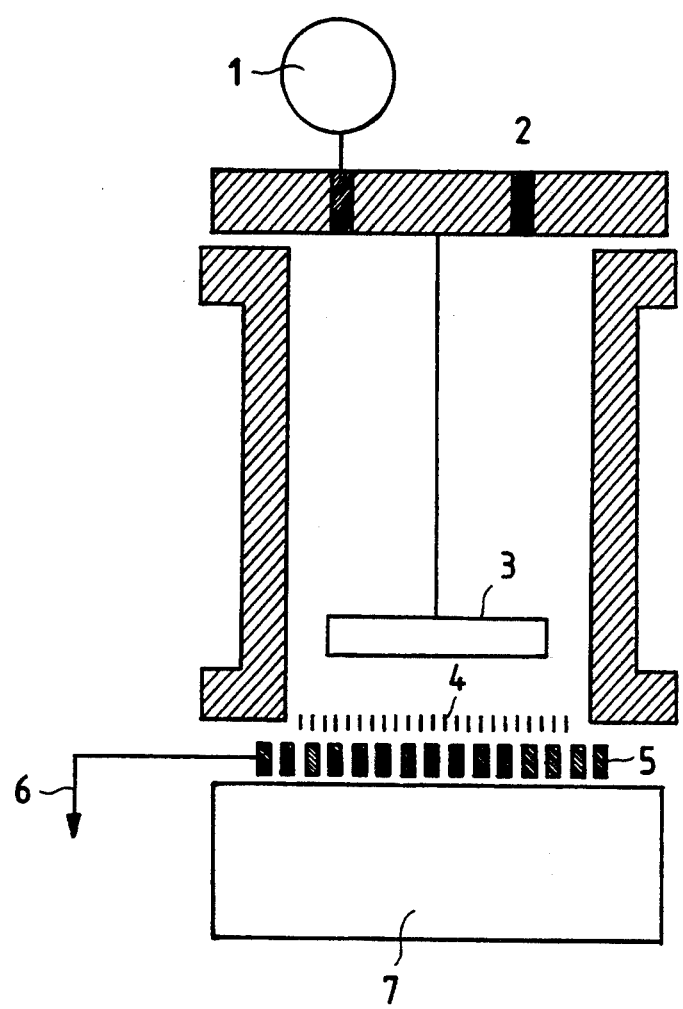
FIG. 1 shows an ultrafiltration system.

The ultrafiltration system displayed in FIG. 1 consists of a stainless steel cell of 0.5 l of capacity, stirred by means of a overhanging magnetic bar (3) driven by a driving motor means (7). The necessary pressure is supplied by means of nitrogen delivered from the inlet (2) and is checked by means of the pressure gauge (1). The ultrafiltration membrane (4) is laid on the support (5) connected with the permeate manifold (6).

The filtering surface area is of about 20 cm².

In that way, membranes of FS61PP ® (type membrane manufactured by DDS-DOW SEPARATION SYSTEMS (DK) and constituted by fluorinated polymers); and membranes of CARBOSEP ® (type membrane, manufactured by Rh(o)ne Poulenc, constituted by aluminum oxides and preferably graphite and metal oxides) were selected for their capability of retaining (=rejecting) the dissolved catalyst in an organic phase. The nominal exclusion limits of the selected membranes were comprised within the range of from 5,000 to 50,000 Da.

The efficiency of a separation process carried out by means of the use of semipermeable membranes can be expressed by the rejection R defined as:

$$R = 1 - Ca/Cp$$

wherein:
  Ca = initial concentration of metal to be separated;
  Cp = metal concentration in the permeate stream.

In general, the systems applied in industry, in order to reach high efficiency values, are of tangential ultrafiltration type: in practice, the treated fluid is pumped at a high speed, tangentially relatively to the filtering surface.

For this system type, several geometries are available, as: flat membranes, membranes in spiral arrangement, hollow fibres, tubular membranes. The selection is dictated by the physical-chemical characteristics of the fluid to be submitted to the treatment (e.g., amount of suspended solid matter, viscosity and chemical composition).

The process according to the present invention also comprises using a tangential ultrafiltration system equipped with tubular membranes of CARBOSEP ®.

Such membranes meet the required conditions for industrial use, which are:
  strength to withstand external physical forces;
  resistance to chemical agents;
  resistance to microorganisms;
  resistance to high temperatures;
  easy of washing, so as to restore the fluxes;
  long useful operating life;
  low costs.

Figure 2:
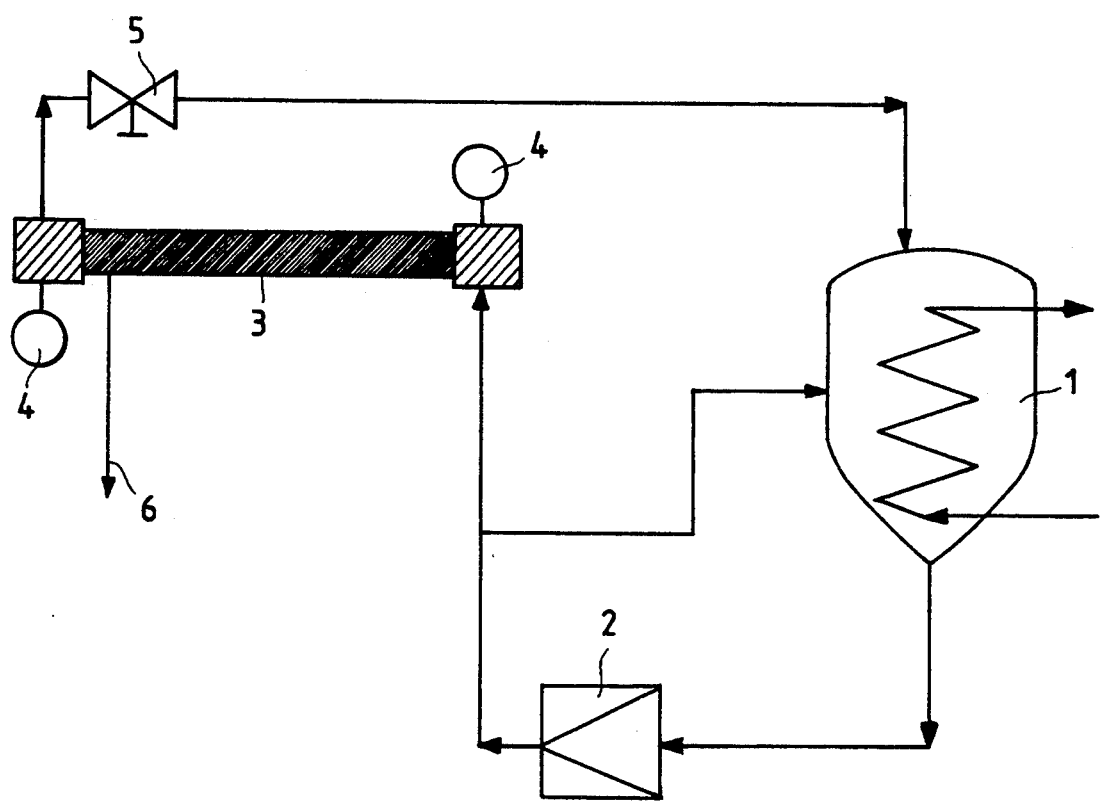
FIG. 2 shows a tangential ultrafiltration system.

The tangential ultrafiltration system displayed in FIG. 2 comprises a heated tank (1); a metering gear pump model G4 (PULSAFEEDER, Rochester N.Y.) (2); a tubular ultrafiltration membrane of CARBOSEP ® (RHONE-POULENC ITALIA SpA, Milan) with container (3); pressure gauges for checking the module inlet and module outlet pressure (4); a pressure control valve (5) and a permeate outlet (6).

The catalysts which can be separated by means of the process according to the present invention are tetra alkyl ammonium or tetra alkyl phosphonium tetra (diperoxo tungsto) phosphates (or arsenates) and, in particular,

* dimethyl[dioctadecyl(76%)+dihexadecyl(24%)]ammonium tetra(diperoxo tungsto)phosphate $PW_4O_{24}(C_{38}H_{80}N)_3$ (76 mol %), $PW_4O_{24}(C_{34}H_{72}N)_3$ (24 mol %); and

* [tributyl(n-hexadecyl)]phosphonium tetra(diperoxo tungsto)phosphate, $PW_4O_{24}(C_{28}H_{60}P)_3$, prepared as disclosed in EP-A-225 990 and generally present in the reaction mixtures at concentrations comprised within the range of from 0.01 to 5%.

In the tangential ultrafiltration system, the recycle flow rate is usually so regulated as to keep the linear velocity comprised within the range of from 1 to 10 m.seconds$^{-1}$ and preferably of from 2 to 5 m.seconds$^{-1}$, respectively corresponding to 170 and 430 L.h$^{-1}$ for the modules disclosed in the following.

The operating pressure range is comprised within the range of from 0.1 to 1 MPa.

The mixture can be fed at temperatures comprised within the range of from 0° to 250° C.

The permeate flow rate is generally comprised within the range of from 1 to 50 Lm²h$^{-1}$.

The analysis of the permeate demonstrates tungsten concentration lower than 0.03%.

Some examples follow, which are supplied in order to illustrate the invention without limiting it.

EXAMPLE 1

The catalyst (0.94 g) composed by a mixture of: tri[(di-n-hexadecyl)dimethyl]ammonium tetra(diperoxo tungsto)phosphate $PW_4O_{24}(C_{34}H_{72}N)_3$ (76 mol %) and $PW_4O_{24}(C_{38}H_{80}N)_3$ (24 mol %) (0.94 g), separately prepared as disclosed in EP-A-225 990, is dissolved in a mixture (0.5 l) of internal alkenes (distillation cut $C_{13}$-$C_{14}$). The concentration of W in this solution is of 5,500 mg.l$^{-1}$. The solution is submitted to ultrafiltration in the static cell device disclosed in FIG. 1, equipped with polymeric membrane FS61PP ® (Dow Separation System), having an exclusion molecular weight of 20 kDa. The pressure is kept comprised within the range of from 0.5 to 0.6 MPa with nitrogen. After causing 0.1 liter of solution to permeate, a concentration of W in the permeate of 2,000 mg.l$^{-1}$ is obtained, and in the retentate, the concentration of W results to be of 6,000 mg.l$^{-1}$.

EXAMPLE 2

The catalyst (0.94 g) composed by a mixture of: tri[(di-n-hexadecyl)dimethyl]ammonium tetra(diperoxo tungsto)phosphate $PW_4O_{24}(C_{34}H_{72}N)_3$ (76 mol %) and $PW_4O_{24}(C_{38}H_{80}N)_3$ (24 mol %), separately prepared as disclosed in EP-A-225 990, is dissolved in a mixture (0.5 l) of internal alkenes (distillation cut $C_{13}$-$C_{14}$). The concentration of W in this solution is of 5,500 mg.l$^{-1}$. The solution is submitted to ultrafiltration in the previously disclosed static cell device, equipped with polymeric membrane FS81PP ® (Dow Separation System), having an exclusion molecular weight of 6 kDa. The pressure is kept comprised within the range of from 0.5 to 0.6 MPa with nitrogen. After causing 0.25 liter of solution to permeate, a concentration of W in the permeate of 130 mg.l$^{-1}$ is obtained, and in the retentate, the concentration of W results to be of 7,000 mg.l$^{-1}$.

EXAMPLE 3

0.1 liter of organic phase obtained as in the oxidation reaction disclosed in Example 6 is filtered on a fast paper filter. The concentration of W in this solution is of 190 mg.l$^{-1}$. The clear solution is ultrafiltered by means of the static cell device disclosed in FIG. 1, equipped with a polymeric membrane FS81PP ® (Dow Separation System) having an exclusion molecular weight of 6 kDa. The concentration of W in this solution is of 1,900 mg.l$^{-1}$. The pressure is kept at 1.0 MPa with nitrogen. After causing 0.09 l of solution to permeate, a concentration of W in the permeate of 200 mg.l$^{-1}$ is obtained, and in the retentate the concentration of W results to be of 18,100 mg.l$^{-1}$.

EXAMPLE 4

The catalyst dimethyl[dioctadecyl(76%)+dihexadecyl(24%)]ammonium tetra(diperoxotungsto)phosphate (2.82 g), separately prepared as disclosed in EP-A-225 990 is dissolved in a mixture (1.5 l) of internal alkenes (distillation cut $C_{13}$–$C_{14}$). The concentration of W in this solution is of 545 mg.l$^{-1}$.

The solution is submitted to ultrafiltration in the device schematically displayed in FIG. 2, equipped with a tubular membrane CARBOSEP® M5 (Rh(o)ne-Poulenc) having an exclusion molecular weight of 10 kDA, with an inner diameter of 5.5 mm and 600 mm of length. The operating conditions are as follows: recycle flow rate 225 l.h$^{-1}$; pressure at module inlet: 0.35 Mpa; temperature 50° C. During the first step of the operation, the permeate flow rate results to be of 63 l.m$^{-2}$.h$^{-1}$. After that 1.0 l of mixture has permeated, the permeate flow rate results to be of 32 l.m$^{-2}$.h$^{-1}$. The concentration of W in the permeate is lower than 3 mg.l$^{-1}$, and the concentration of W in the retentate is of 1,600 mg.l$^{-1}$, equivalent to a rejection of >99%.

EXAMPLE 5

The catalyst (2.82 g) composed by a mixture of: tri[(di-n-hexadecyl)dimethyl]ammonium tetra(diperoxotungsto)phosphate $PW_4O_{24}(C_{34}H_{72}N)_3$ (76 mol %) $PW_4O_{24}(C_{38}H_{80}N)_3$ (24 mol %), separately prepared as disclosed in EP-A-225 990, is dissolved in a mixture (1.5 l) of 1-alkenes (distillation cut $C_{13}$–$C_{14}$). The concentration of W in this solution is of 152 mg.l$^{-1}$. The solution is submitted to ultrafiltration in the device schematically displayed in FIG. 2, equipped with a tubular membrane CARBOSEP® M2 (Rh(o)ne-Poulenc) having an exclusion molecular weight of 15 kDA, with an inner diameter of 6 mm and 600 mm of length. The operating conditions are as follows: recycle flow rate 225 l.h$^{-1}$; pressure at module inlet: 0.35 Mpa; temperature 50° C. During the first step of the operation, the permeate flow rate results to be of 85 l.m$^{-2}$.h$^{-1}$. After that 1.12 l of mixture has permeated, the permeate flow rate results to be of 55 l.m$^{-2}$.h$^{-1}$. The concentration of W in the permeate is lower than 3 mg.l$^{-1}$, and the concentration of W in the retentate is of 615 mg.l$^{-1}$.

EXAMPLE 6

2,000 g of a mixture of linear internal alkenes (distillation cut $C_{13}$–$C_{14}$), 31 g of catalyst, which is tri[(di-n-hexadecyl)dimethyl]ammonium tetra(diperoxotungsto)phosphate $PW_4O_{24}(C_{34}H_{72}N)_3$, and 584 g of distilled water are charged to a glass reactor of 5,000 ml, equipped with mechanical stirrer, reflux condenser, thermometer and dripping funnel, and provided with an external cooling jacket. The temperature of the mixture is increased up to 75° C. and then 1,065 ml of $H_2O_2$ at 38.42% (0.6 mol) are added dropwise at such a flow rate that the temperature remains comprised within the approximate range of from 71° to 75° C.

When addition is ended, the mixture is kept stirred for a further 7 hours. The reaction mixture is cooled down to room temperature and is allowed to rest until a phase separation is obtained. The aqueous phase is separated and then is discarded. 2,182 g of an oily liquid with a content of W of 3,310 mg.l$^{-1}$ is obtained.

A portion of this solution (1.5 l) is submitted to ultrafiltration in the device displayed in FIG. 2, equipped with a tubular micro membrane CARBOSEP® 60 M2 with rated exclusion molecular rate 15,000 Da. The operating conditions are as follows: recycle flow rate 280 l.h$^{-1}$; module inlet pressure: 0.35 MPa; temperature 54° C. During the first operation step, the flow rate of permeate results to be of 6.0 m$^{-2}$h$^{-1}$. After that 0.5 l of mixture have permeated, the flow rate of the permeate results to be of 5.5 l m$^{-2}$h$^{-1}$, and the concentration of W in the permeate results to be of 110 mg.l$^{-1}$, and the concentration of W in the retentate is of 4,700 mg.l$^{-1}$, corresponding to a rejection of 97%.

EXAMPLE 7

104.4 g of soybean oil, having an iodine number of 136 (corresponding to a maximum epoxy number of 7.9) and 0.9 g of trioctyl methyl ammonium tetra(diperoxotungsto)phosphate $PW_4O_{24}(C_{25}H_{54}N)_3$ are charged to a 4-necked flask of 250 ml, equipped with mechanical stirrer, reflux condenser, thermometer and dripping funnel. The temperature of the mixture is increased up to 60° C. and then 53.1 ml of $H_2O_2$ at 38.42% (0.6 mol) is added dropwise with strong stirring, at such a flow rate that the internal temperature remains approximately constant.

After the addition, the mixture is kept with stirring for a further 7 hours. The reaction mixture is cooled down to room temperature, and then n-hexane is added, so that a phase separation is obtained. The organic phase is separated and the solvent is evaporated under vacuum. 111.8 g is obtained of an oil characterized by an iodine number of 2.7 and an epoxy number of 7.0. The resulting solution, containing 2,400 mg.ml$^{-1}$ of W, is submitted to ultrafiltration by means of the device disclosed in FIG. 2, equipped with a tubular membrane CARBOSEP® M2. The operating conditions are as follows: recycle flow rate 278 l.h$^{-1}$; module inlet pressure: 0.40 MPa; temperature 105° C.

A permeate with a concentration of W of 123 ppm, equivalent to a rejection of 95% is obtained.

We claim:

1. An ultrafiltration process for separating catalyst(s) from an organic solution in which the catalyst or catalysts are dissolved, the catalyst(s) consisting essentially of phosphotungstates or arsenotungstates as an anionic portion and ammonium or phosphonium salts as a counter-ion having surfactant characteristics, which process comprises the step of passing the catalyst-containing organic solution through an ultrafiltration membrane having an exclusion molecular weight sufficient to retain some of the catalyst(s) and to form, as a permeate, an organic solution containing a reduced concentration of the dissolved catalyst(s) and, as a retenate, an organic solution having an increased concentration of the dissolved catalyst(s).

2. Process according to claim 1, wherein the ultrafiltration membrane is based on aluminum oxides or graphite and metal oxides.

3. Process according to claim 1, wherein the ultrafiltration membrane is based on fluorinated polymers.

4. Process according to claim 1, wherein the ultrafiltration membrane has an exclusion molecular weight of from 5,000 to 50,000 Da.

5. Process according to claim 4, characterized in that the ultrafiltration wherein the ultrafiltration membrane has an exclusion molecular weight of from 10,000 to 15,000 Da.

6. Process according to claim 1, wherein the organic solution containing the dissolved catalyst is filtered before passing the solution through the ultrafiltration membrane.

7. Process according to claim 1, wherein the organic solution is an alkene solution.

8. Process according to claim 1, wherein the organic solution is a reaction mixture obtained from a homogeneous catalytic epoxidation of alkenes.

9. Process according to claim 1, wherein the organic solution is a reaction mixture obtained from a homogeneous catalytic epoxidation of soybean oil.

10. Process according to claim 1, wherein the temperature of the organic solution is kept at values from 0° to 250° C.

11. Process according to claim 1, wherein the catalyst concentration is from 100 to 20,000 mg.l$^{-1}$ in the retenate and from 0 to 150 mg.l$^{-1}$ in the permeate.

12. Process according to claim 1, wherein the process is carried out in a tangential ultrafiltration device.

13. Process according to claim 1, wherein the catalyst is selected from the group consisting of tri[(di-n-hexadecyl)-dimethyl]ammonium tetra(diperoxotungsto)phosphate, tri[(di-n-hexadecyl)-dimethyl]ammonium tetra(diperoxotungsto)arsenate, trioctyl methyl ammonium tetra(diperoxotungsto)phosphate, trioctyl methyl ammonium tetra(diperoxotungsto)arsenate, [tributyl(n-hexadecyl)]phosphonium tetra(diperoxotungsto)phosphate, [tributyl(n-hexadecyl)]phosphonium tetra(diperoxotungsto)arsenate, and mixtures thereof.

14. Process according to claim 1, wherein the process is carried out in a tangential ultrafiltration device equipped with a tubular membrane and wherein the permeate is recycled.

15. Process according to claim 14, wherein the permeate flow rate is from 10 to 50 m.$^3$.h$^{-1}$ per each m$^2$ of membrane surface.

16. Process according to claim 14, wherein the process is carried out under pressure in a tangential ultrafiltration device; wherein the ultrafiltration membrane is flat or tubular and has an exclusion molecular weight of from 5000 to 50,000 Da.

17. Process according to claim 16, wherein the operating pressure is from 0.1 to 1 MPa.

18. Process according to claim 14, wherein the recycle flow rate linear velocity is from 1 to 10 m.s$^{-1}$.

* * * * *

UNITED STATES PATENT AND TRADEMARK OFFICE
CERTIFICATE OF CORRECTION

PATENT NO. : 5,350,521

DATED : September 27, 1994

INVENTOR(S) : Nunzio Andriollo et al.

It is certified that error appears in the above-identified patent and that said Letters Patent is hereby corrected as shown below:

TITLE PAGE, ITEM [73]:

Please change Assignee from "Eniricerche, S.p.A., Milan, Italy" to --Enichem, SpA, Milan, Italy--.

Signed and Sealed this

Twenty-third Day of May, 1995

Attest:

BRUCE LEHMAN

Attesting Officer

Commissioner of Patents and Trademarks